(12) United States Patent
Friedman

(10) Patent No.: US 7,097,452 B2
(45) Date of Patent: Aug. 29, 2006

(54) HEATED COMPULE

(76) Inventor: Joshua Friedman, P.O. Box 2867, Danbury, CT (US) 06810

( * ) Notice: Subject to any disclaimer, the term of this patent is extended or adjusted under 35 U.S.C. 154(b) by 0 days.

(21) Appl. No.: 10/987,203

(22) Filed: Nov. 13, 2004

(65) Prior Publication Data

US 2005/0186532 A1 Aug. 25, 2005

Related U.S. Application Data

(63) Continuation-in-part of application No. 10/783,924, filed on Feb. 20, 2004.

(51) Int. Cl.
*A61C 5/04* (2006.01)
(52) U.S. Cl. ........................................ 433/90
(58) Field of Classification Search ............... 433/89, 433/90, 32; 222/146.5, 325, 326, 327
See application file for complete search history.

(56) References Cited

U.S. PATENT DOCUMENTS

| 4,704,088 | A  | * | 11/1987 | Newman ..................... 433/81 |
| 6,689,835 | B1 | * | 2/2004  | Amarasekera et al. ...... 524/495 |
| 2003/0165793 | A1 | * | 9/2003 | Yobel et al. ................. 433/90 |

* cited by examiner

*Primary Examiner*—John J. Wilson
*Assistant Examiner*—Meoghan E. MacPherson

(57) ABSTRACT

A compule for storing dental composite material to be extruded from the compule using a standard dispenser in the preparation or repair of a dental restoration. The compule comprises: a cylindrical body having an orifice at one end thereof through which the dental composite material is extruded and a means at the opposite end thereof to facilitate the extrusion of said dental composite material using the dispenser. The body of the compule is composed of an electrically conductive plastic or alternatively may be composed of a thermally and electrically conductive plastic having a thermal conductivity in the range of between 1.0 w/mk and 500 w/mk and an electrical resistivity in the range 0.01–10,000 ohm-cm.

6 Claims, 2 Drawing Sheets

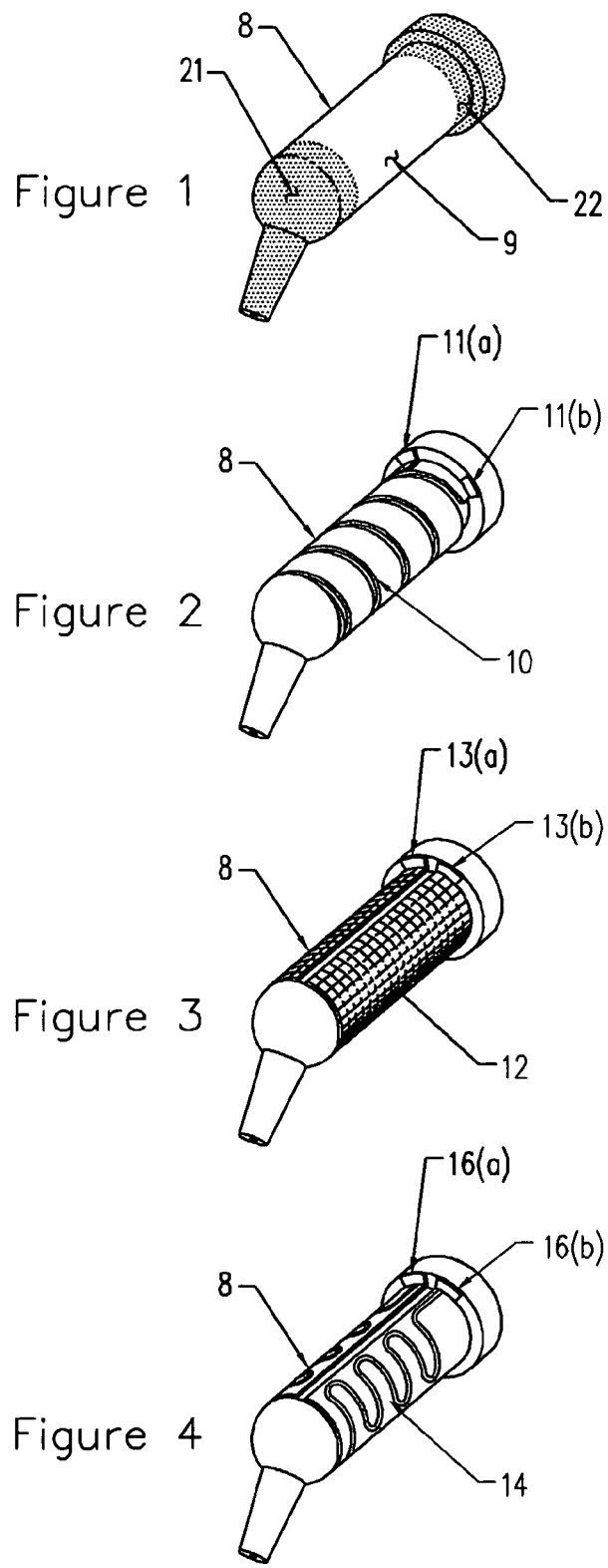

HEATED COMPULE

FIELD OF INVENTION

This invention is a continuation in part of U.S. patent application Ser. No. 10/783,924 filed Feb. 20, 2004 and relates to a compule for storing dental composite material and more particularly to a dental compule which is thermally conductive and preferably also electrically conductive so that the composite material can be heated quickly by direct heat transfer upon heating the compule.

BACKGROUND

Light cured materials have become regularly used in dentistry. The advantages of light curing a one-part material over a two-part system are well documented. The ability to cure on command offers the dental practioner a wide degree of control over the shape and shade of a dental restoration. This inventor has discussed various methods of delivering heated dental materials, which because of the heating effect causes these materials to take on superior handling characteristics as well as improved physical properties in the polymerized state.

In the case of dental composite fillings, all these methods relate to either heating them in syringes, in compules in which they are delivered or simply heating the material directly in an external device.

New research on dental materials has shown many benefits to heating these materials prior to polymerization. Demonstrated advantages are as follows:

1. Substantially faster monomer conversion (shorter curing time) (IADR—0819 Thermal Effects on Composite Photopolymerization Monitored by Real-time NIR By Drs. M. Trujillo and J. W. Stansbury, University of Colorado Health Sciences Center, Denver, Colo., USA).
2. Greatly reduced viscosity (IADR—Composite Film Thickness at Various Temperatures By Drs. R. G. Holmes, J. S. Blalock, and F. A. Rueggeberg, Medical College of Georgia, Augusta, Ga. USA).
3. Much greater material flow offering better adaptation to tooth surface (Dr. Broome, Associate Professor, University of Alabama School of Dentistry, Birmingham, Ala., USA) Report to AdDent Quantification of Flow Increase Resulting from Preheating Composite Compules dated Jun. 6, 2003).

Recently, research has also shown that when a composite is preheated, we can achieve much less microleakage at the cervical margin of a dental restoration (IADR—Effect of Pre-Heating Composite on Microleakage in Class II Restorations By M. N. Aksu, A.-M. L. Neme, S. Walker, F. E. Pink, J. B. Linger, and W. C. Wagner, University of Detroit Mercy, Mich., USA). Microleakage is a major factor in causing decay under a dental restoration.

The use of heated dental restorative materials has been described in U.S. Pat. Nos. 6,236,020 and 6,616,448. A method for using heated dental materials has been described in U.S. Pat. No. 6,320,162. In both of these earlier applications, I described a method and a device for heating dental materials. In the devices used in my previous applications, a widely used compule that stores the material is heated externally. One method uses a heater placed in a block of thermally conductive material another method uses a heating element embedded in a molded plastic holder that is also part of a means for dispensing material.

Previous attempts to warm dental materials have either done so in a laboratory oven or in the container it is packaged in such as a syringe or compule. While these methods work for introducing heated composite materials into the mouth, they suffer from several drawbacks. In the case of heating a syringe, a large bulk of material is heated needlessly, and the heating time is long. In the case of heating a compule (dose package), the heating time is shortened but still significantly long. In the case of heating material expressed from a syringe onto a heated surface, the material needs to be first picked up, then introduced into the dental cavity and then repeated with each layer, also in a time consuming procedure. The invention described herein eliminates these drawbacks. In this invention, the heat is generated directly within the compule itself, and in so doing, creates a very efficient method of heat transfer from the source of heat directly into the material to be heated.

Many dentists have found it useful and convenient to dispense restorative composite, root canal filling materials; dental bleach as well as dental sealants and coatings directly from a pre dosed compule. Currently, the various compules on the market are made from polyethylene either high (HDP) or low density (LDP) as well as other commonly used plastics.

SUMMARY OF THE INVENTION

The dental compule of the present invention is fabricated from a thermally conductive plastic having a thermal conductivity in the range from 1.0 w/mk to 500 w/mk. Such materials of themselves are known and commercially available. One such material is COOLPOLY D5104 a trademark product of Cool Polymers, Inc. USA for an electrically conductive material. A compule formed from a thermally conductive material having a thermal conductivity in the range from 1.0 w/mk to 500 w/mk will cause a dental composite restorative material stored in the compule to be heated up two or three times faster than it would even under conditions described in U.S. Pat. Nos. 6,236,020, 6,616,448 and 6,320,162.

An improved compule of the present invention incorporates a molded in (insert molded) heating means into the thermally conductive body of the compule so that the compule will be both thermally conductive and electrically conductive. In a preferred embodiment, the plastic itself is made from a class of materials, which is both thermally and electrically conductive with electrical conductivity measured as resistivity in the range 0.01–10,000 ohm-cm. One such material may be the COOLPOLY E5101 a trademark product of Cool Polymers, Inc. USA for a polymeric composition which is both electrically and thermally conductive. In this preferred embodiment the heating material is formed into distinct sections, i.e., half sections (although it is not critical that each section be identical in size) which surround the body of the compule or define the body of the compule and an electrical current is passed through both halves of the compule so that the plastic itself will heat up. Since the compule is now itself the heating element, heating is much more efficient and the material heats significantly faster.

Using this arrangement, there is more than an order of magnitude (i.e. 10 seconds compared to 180 seconds) reduction in heating time. In addition, the power required is far less, making the dispensing device, smaller, less costly and easier to handle.

There are a number of configurations that can be used to accomplish the heating of a dental compule in accordance with the present invention. As explained above the compule itself may be composed of a thermally conductive plastic preferably having a thermal conductivity in the range from 1.0 w/mk to 500 w/mk to provide for better heat transfer. Other iterations include heating elements either molded into or adhered to the surface of the compule body. Heating elements are generally conductive materials that provide some electrical distance which when placed in a circuit connected to a power source produce a heating effect proportional to the resistance and the current flowing in the circuit. FIGS. 1 through 5 show various ways of achieving this condition.

BRIEF DESCRIPTION OF DRAWINGS

FIG. 1 shows a perspective view of a compule of the present invention for storing dental material;

FIG. 2 shows another embodiment of the compule of the present invention;

FIG. 3 is a perspective view of yet another embodiment of the compule of the present invention;

FIG. 4 shows a perspective view of a further embodiment of the compule of the present invention.

DETAILED DESCRIPTION OF THE INVENTION

Figure 5A:
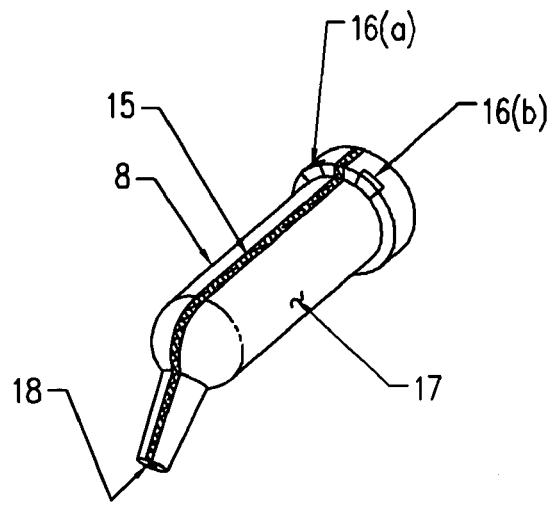
FIGS. 5(a–c) show different views of the compule of the present invention.

FIG. 1 is a perspective view of the compule (8) of the present invention with the body (9) of the compule (8) composed of thermally conductive plastic having a thermal conductivity in the range from 1.0 w/mk to 500 w/mk. It should be understood that the word compule is be interpreted broadly for purpose of the present application to represent any conventional container to store dental material such as dental composite adapted for use with a standard dispensing device to express the dental material from the compule and includes that of a dental syringe.

FIG. 1 also shows the use of an electrically conductive material to form the body (9) of compule (8). The body material (9) has a resistivity in the range of 0.01–10,000 ohm-cm. Once electrical contact is made anywhere on or along the distal area (21) adjacent the dispensing end of the compule (8) and the other electrical contact is made anywhere on or along the proximal area (22). The areas 21 and 22 are identified in FIG. 1 as shaded areas and designate arbitrary areas at each opposite end of the compule for placement of electrical contacts for connection to an external source of power.

FIG. 2 shows a perspective view of the compule (8) with an electrical heating element (10) insert molded in a spiral pattern onto its surface or internally situated. The element (10) can be made from Nichrome Wire, Steel, Silver or Copper conductor or any electrically conductive material. Electrical contacts (11a,11b) connect the heating element (10) to an external power source (not shown).

FIG. 3 shows a perspective view of a compule (8) using a conductive carbon fabric to form a heating element 12. The heating element (12) adheres to the compule outer surface or is internally molded or internally situated. A pair of electrical contacts (13a,13b) is connected to the heating element (12) at opposite ends thereof for forming a series electrical circuit for resistive heating of the element (12) when the electrical contacts (13a, 13b) are connected to an external power source (not shown).

FIG. 4 shows a perspective view of a compule (8) with a flexible circuit consisting of a printed conductor layered either directly on the compule or adhered to a plastic film that is bonded to the compule surface. Electrical contacts (16a,16b) connect to the heating element (14) and to a power supply (not shown).

Figure 5B:
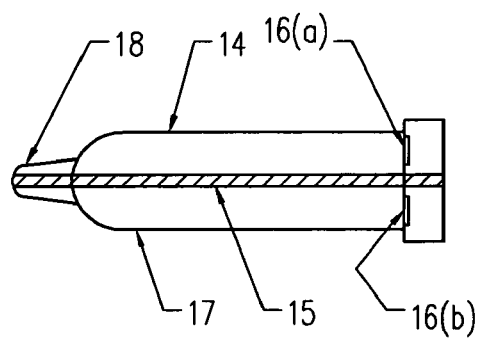
Figure 5C:
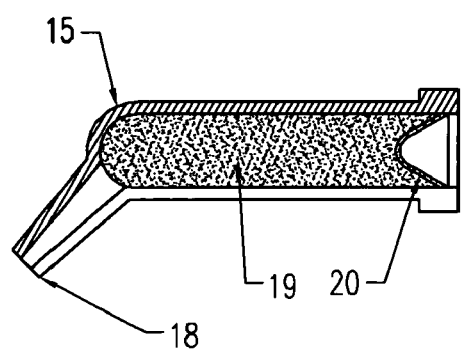

FIG. 5 (a) is another perspective view of the compule (8). An insulating plastic (15), that is electrically nonconductive, extends lengthwise along the body of the compule (8) for forming an insulating divide separating an electrically conductive plastic (17) which itself constitutes both a heating element and a thermally conductive plastic into sections. The electrically conductive plastic (17) may surround the body of the compule (8) or be internally molded or situated or itself become the body of the compule (8) Electrical contacts (16a,16b) are connected to the separated sections of the heating element (17) and to a power source (not shown).

What I claim is:

1. A compule for storing and heating dental composite material to be extruded from the compule using a dispenser in the preparation or repair of a dental restoration, said compule comprising:

a body for enclosing the dental composite material, said body having opposite ends, an outlet orifice at one end thereof through which the dental composite material is extruded and a head adapted at the opposite end thereof to facilitate the extrusion of said dental composite material using said dispenser, said body being composed of an electrically conductive and a thermally conductive plastic having a resistivity in a range of between 0.01 and 10,000 ohm-cm and a thermal conductivity in the range of between 1.0 w/mk and 500 w/mk and having a contact area located substantially at each opposite end of the compule for electrically connecting each contact area to an external source of power so that the said dental composite material can be quickly heated by directly passing current through the body of the compule from each of said opposite ends.

2. A compule as defined in claim 1 wherein said body is cylindrical in configuration.

3. A compule for storing and heating dental composite material to be extruded from the compule using a dispenser in the preparation or repair of a dental restoration, said compule comprising:

an elongated body of predetermined length for enclosing the dental composite material between opposite ends of said body with said body being composed of an electrically and thermally conductive plastic material composition having an outlet orifice at one end thereof through which the dental composite material is extruded and a head adapted at the opposite end thereof to facilitate extruding said dental composite material from said compule using said dispenser, said compule further comprising opposite sides and an insulating spacer extending longitudinally from one end of the body to the opposite end and located on only one of said opposite sides for dividing the body into a first part and second part respectively on each opposite side of said insulating spacer and further comprising a first contact area or contact terminal for said first part and a second contact area or contact terminal for said second part with each contact area or contact terminal adapted to electrically connect said first and second part of said body to an external source of power so that said dental composite material can be quickly heated by directly passing current through said contact areas or terminals.

4. A compule as defined in claim 3 wherein said body is cylindrical in configuration.

5. A compule as defined in claim 4 wherein each of said first two parts have a resistivity in a range between 0.01 and 10,000 ohm-cm and a thermal conductivity in the range of between 1.0 w/mk and 500 w/mk.

6. A compule as defined in claim 5 wherein each contact area or contact terminal in each part of said body is disposed at a given end of said body.

* * * * *